US010246644B2

(12) United States Patent
Du et al.

(10) Patent No.: US 10,246,644 B2
(45) Date of Patent: *Apr. 2, 2019

(54) METHOD FOR PREPARING BIODIESEL

(75) Inventors: Wei Du, Beijing (CN); Dehua Liu, Beijing (CN); Luole Zhu, Beijing (CN)

(73) Assignee: Tsinghua University, Beijing (CN)

( * ) Notice: Subject to any disclaimer, the term of this patent is extended or adjusted under 35 U.S.C. 154(b) by 954 days.

This patent is subject to a terminal disclaimer.

(21) Appl. No.: 14/005,038

(22) PCT Filed: Nov. 29, 2011

(86) PCT No.: PCT/CN2011/083130

§ 371 (c)(1),
(2), (4) Date: Jan. 10, 2014

(87) PCT Pub. No.: WO2012/122826

PCT Pub. Date: Sep. 20, 2012

(65) Prior Publication Data

US 2014/0123544 A1 May 8, 2014

(30) Foreign Application Priority Data

Mar. 15, 2011 (CN) .......................... 2011 1 0062697

(51) Int. Cl.

*C10G 3/00* (2006.01)
*C10L 1/02* (2006.01)
*C11C 3/00* (2006.01)
*C12P 7/64* (2006.01)

(52) U.S. Cl.

CPC ................ *C10G 3/00* (2013.01); *C10L 1/026* (2013.01); *C11C 3/003* (2013.01); *C12P 7/649* (2013.01); *C10L 2200/0476* (2013.01); *C10L 2290/26* (2013.01); *C10L 2290/548* (2013.01); *Y02E 50/13* (2013.01); *Y02P 30/20* (2015.11)

(58) Field of Classification Search

None

See application file for complete search history.

(56) References Cited

FOREIGN PATENT DOCUMENTS

| | | | |
|---|---|---|---|
| CN | 101113360 | | 1/2008 |
| CN | 101358216 | | 2/2009 |
| CN | 101381614 | | 3/2009 |
| CN | 101418322 A | * | 4/2009 |
| CN | 100494316 | * | 6/2009 |
| CN | 101358216 | * | 11/2011 |
| WO | WO2010047480 A2 | | 4/2010 |

OTHER PUBLICATIONS

International Chinese Search Report issued in corresponding International Application No. PCT/CN 2011/ 083130 dated Mar. 15, 2012.

* cited by examiner

*Primary Examiner* — Sharmila G Landau
*Assistant Examiner* — Stephen M Chong
(74) *Attorney, Agent, or Firm* — Haug Partners LLP

(57) ABSTRACT

The present invention provides a method for preparing biodiesel, comprising: adding oil and fat, short-chain alcohol, water, and liquid lipase into a single-stage or multi-stage enzyme reactor; then separating the reaction fluid into an enzyme-containing heavy phase and a light phase; recovering and reusing the enzyme in the heavy phase; using the light phase for subsequent conversion by immobilized lipase; flowing the light phase and the short-chain alcohol into single-stage or multi-stage enzyme reactor containing an immobilized lipase; performing online dehydration during the whole reaction process or part of the reaction process. In the method of the invention for preparing biodiesel, no preprocessing is required for the oil and fat feedstock in the earlier stage of catalysis process by liquid lipase, and the conversion ratio from oil and fat to biodiesel can reach more than 90%; in the later stage of catalysis process by immobilized lipase, by introducing an online dehydration during the whole process or part of the reaction process, the yield of biodiesel can exceed 98%, and the acid value of the product can be less than 0.5 mg KOH per gram of oil. The method thus has good economic and environmental benefits.

10 Claims, 2 Drawing Sheets

METHOD FOR PREPARING BIODIESEL

TECHNICAL FIELD

Figure 1:
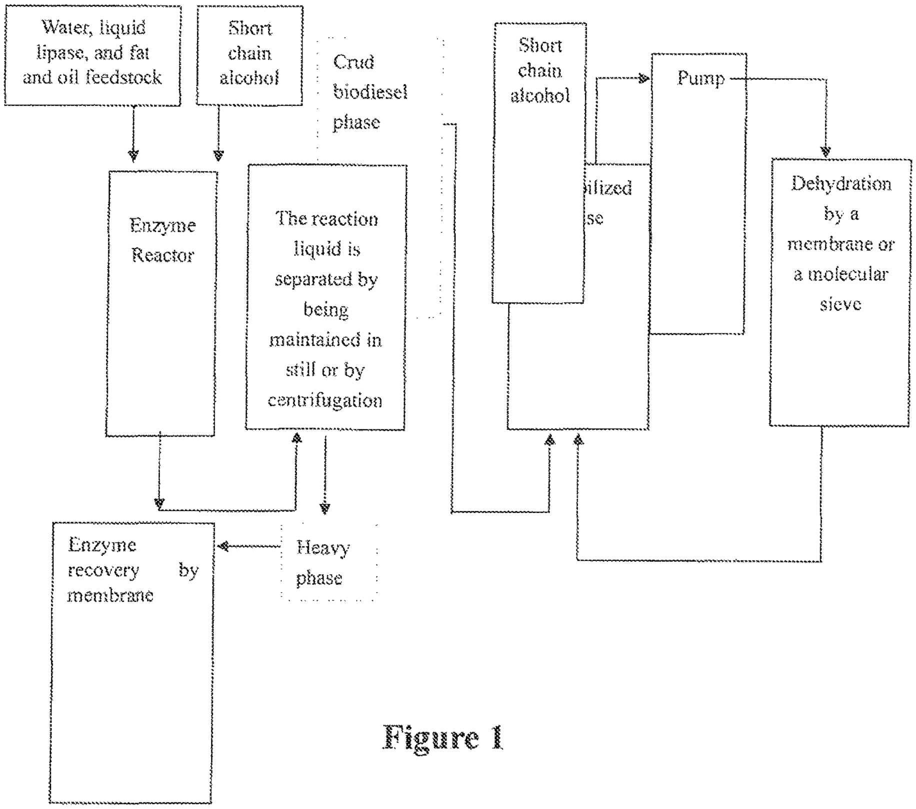

The present invention belongs to the technical field of biofuel synthesis, in particular, it relates to a method for preparing biodiesel using a liquid lipase in combination with an immobilized lipase.

BACKGROUND

Biodiesel are long-chain fatty acid ester substances generated by transesterification reaction of biological oil and fat feedstock. It is a novel renewable energy resource without pollution, and has broad application prospects in oil and fat industry. The combustion properties of biodiesel are comparable to traditional petroleum diesel, and the harmful substances in the exhaust emitted from an engine in which biodiesel is combusted is 50% reduced when compared to traditional petroleum diesel. Currently, extensive attention has been drawn to the investigations and applications of biodiesel.

Currently, biodiesel is primarily produced by chemical processes, i.e. using animal/plant oil and fat together with some low carbon alcohols (methanol or ethanol) to conduct, transesterification reaction under the catalysis of acidic or alkaline catalysts, so as to generate corresponding fatty acid methyl ester or ethyl ester. There exist the following disadvantages when using chemical processes to prepare biodiesel: (1) the free fatty acids and water in the oil and fat feedstock severely affect the progression of the reaction; (2) the poor solubility of methanol in oil and fat would easily result in the formation of emulsion, such that the subsequent processing procedure will become complicated; and (3) the amount of methanol used according to the requirements of the process greatly exceeds the molar ratio of the reaction, and the recovery of the excess methanol increases the energy consumption during the process.

A process using a biological enzyme for synthesizing biodiesel has the following advantages: mild reaction conditions, no pollutant emitted, and broad applicability for various oil and fat feedstock. Such process is in accordance with the green chemistry trend, and thus is getting increasing attention. However, in conventional lipase-catalyzing processes of converting oil and fat feedstock for the preparation of biodiesel, there exists the following problem, when the water content in the oil and fat feedstock is greater than 0.5% (based on the weight of the oil), the acid value of the biodiesel product after the reaction is generally higher than 0.5 mg KOH per gram of oil. This does not fulfill the acid value standard required for biodiesel quality control, and thus subsequent processing procedures involving complicated alkaline neutralization are required. However, such subsequent, processing procedures using alkaline neutralization to decrease the acid value affects the yield of the product, and can bring about pollution problems. Accordingly, it is desired to develop an efficient and environment-friendly method for preparing biodiesel.

CONTENT OF THE INVENTION

The purpose of the invention is to provide a novel method for preparing biodiesel, in particular, the invention provides a novel method for preparing biodiesel using a liquid lipase in combination with an immobilized lipase.

For the purpose of the invention, a method for preparing biodiesel according to the invention comprises the following steps: (1) oil and fat, short chain alcohol, water, and liquid lipase are added into a single-stage or multi-stage reactor for conducting a reaction, and the reaction liquid is then separated into a heavy phase and a light phase; the enzyme in the heavy phase is recovered and reused, and the light phase is used for subsequent conversion by immobilized lipase; (2) the light phase obtained in step (1) is flowed into a single-stage or multi-stage reactor containing immobilized lipase, and short chain alcohol is added for conducting a reaction; an online dehydration is carried out during the whole reaction process or part of the reaction process.

The purpose of the invention can also be accomplished by the following technical means.

Figure 2:
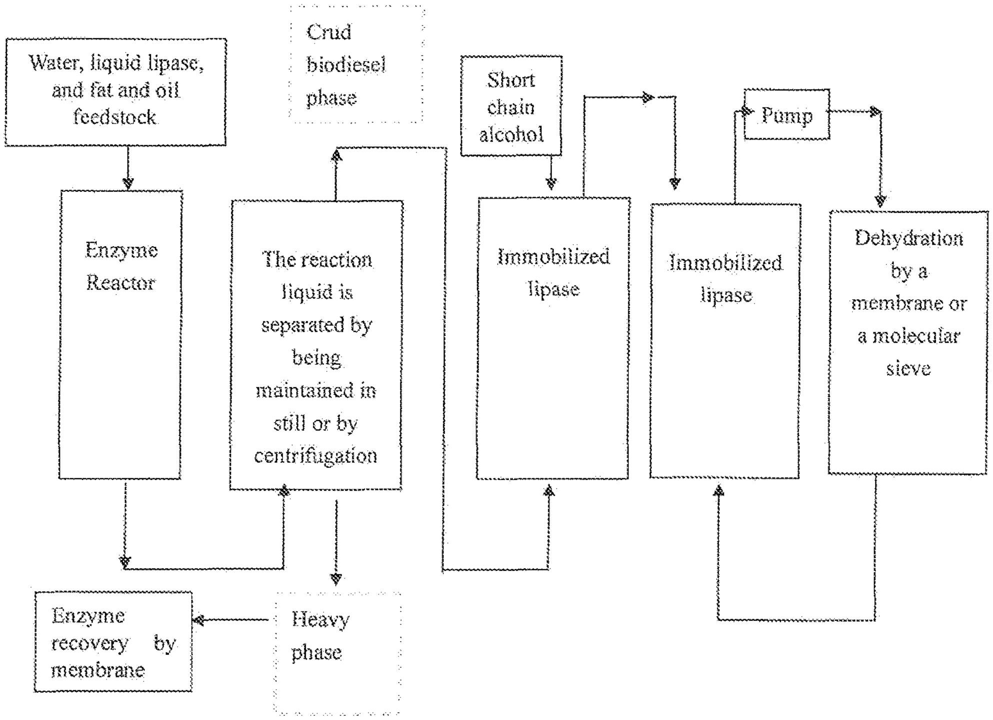

The above-mentioned method for preparing biodiesel using a liquid lipase in combination with an immobilized lipase comprises the following steps: (1) oil and fat, 4-8 times of short chain alcohol based on the mole of the oil and fat, 2%-20% of water based on the mass of oil and fat, and 200-2000 standard active units of liquid lipase based on each gram of the mass of oil and fat are added into the single-stage or multi-stage reactor; the temperature is maintained at 30-55° C.; and the reaction is conducted for 3-8 hours; (2) after the reaction liquid is stratified by centrifugation or standing, the enzyme protein in the heavy phase is separated and recovered using a membrane, and the light phase is used for subsequent conversion by immobilized lipase; (3) the light phase obtained in step (2) and 1-3 times of short chain alcohol based on the mole of the oil and fat are reflowed into single-stage or multi-stage reactor containing 200-1000 standard active units of immobilized lipase based on each gram of the mass of oil and fat; the temperature is maintained at 20-55° C.; the reaction is conducted for 3-10 hours; and an online dehydration with a membrane or a molecular sieve is carried out during the whole reaction process or part of the reaction process. The yield for converting effective oil and fat feedstock into biodiesel is higher than 98%, and the acid value in the final biodiesel product is less than 0.5 mg KOH per gram of oil. The schematic diagram, of the reaction process is shown in FIG. 1 and FIG. 2.

In the above-mentioned method, the membrane used for separating and recovering the enzyme protein in step (2) is a metal membrane, an organic membrane, an inorganic membrane, or a ceramic membrane etc.

In the above-mentioned method, the membrane used for the online dehydration in step (3) is an organic membrane, an inorganic membrane, or a ceramic membrane etc.; the molecular sieve used for the online dehydration is a 3 Å or 4 Å molecular sieve etc.

In the above-mentioned method, the lipase is derived from one or more of *Candida antarctica, Thermomyces lanuginosus, Aspergillus niger, Aspergillus oryzae, Rhizomucor miehei*, and *Rhizopus oryzae* etc.

In the above-mentioned method, the short chain alcohol is methanol, ethanol, propanol, or butanol etc.

In the above-mentioned method, the short chain alcohol is being evenly or unevenly fed from the beginning of the reaction, and the feeding is finished in 3-10 hours.

In the above-mentioned method, the oil and fat is biological oil and fat, including vegetable oil, animal fat, or microbial oil. Wherein, the vegetable oil is castor oil, palm oil, colza oil soybean oil, peanut oil, corn oil, cottonseed oil, rice bran oil, *Jatropha* oil, yellow horn oil, or *Jatropha curcas* L. oil etc.; the animal fat is fish oil, tallow, lard, or mutton oil etc.; and the microbial oil is yeast oil or microalgae oil etc.

The oil and fat also includes waste cooking oil or the oil and fat refining waste. Wherein, the waste cooking oil is swill oil or drainage oil etc.; and the oil and fat refining waste is acidified oil etc.

By the above technical solutions, the invention at least has the following advantages and beneficial effects: in the method of the invention for preparing biodiesel using a liquid lipase in combination with an immobilized lipase, no preprocessing is required for the oil and fat feedstock, and the conversion ratio from oil and fat to biodiesel can reach more than 90%; in the later stage of catalysis process by immobilized lipase, by introducing an online dehydration during the whole process or part of the reaction process, the yield of biodiesel can exceed 98%, and the acid value of the product can be less than 0.5 mg KOH per gram of oil. Therefore, the method of the invention for preparing biodiesel has good economic and environmental benefits.

DESCRIPTION FOR THE DRAWINGS

FIG. 1 and FIG. 2 are flow-sheets of preferred examples of the method for preparing biodiesel using a liquid lipase in combination with an immobilized lipase.

SPECIFIC EMBODIMENTS

The following examples are used for illustrating the invention, but not for limiting the scope of the invention.

The reagents and materials used in the following examples are all commercially available products.

Example 1

10 g of soybean oil, 10% of water based on the mass of oil and fat, and 200 standard active units of liquid lipase (derived from *Candida antarctica*) based on the unit mass of oil and fat, were added into single-stage or multi-stage enzyme reactor suitable for enzyme catalysis. The temperature was maintained at 35° C., and ethanol with a molar ratio of 4.5:1 to the oil and fat was evenly added in 3 hours. After 6 hours of reaction, the conversion ratio from effective oil and fat to biodiesel was 90%. Then the reaction liquid was maintained in still for stratification, and enzyme-containing heavy phase and light phase (crude biodiesel phase) were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The crude biodiesel phase was reflowed into immobilized enzyme reactor (containing 200 standard active units of immobilized lipase (derived from *Aspergillus oryzae*) based on the unit mass of oil and fat), and methanol with a molar ratio of 1:1 to the crude biodiesel was simultaneously added. The reaction was conducted, the temperature was maintained at 20° C., and the methanol was evenly added in 1 hour. During the reaction process, the online dehydration as shown in FIG. 1 was conducted (membrane dehydration device including organic membrane, inorganic membrane, or ceramic membrane, and water-absorbing device including 3 Å or 4 Å molecular sieve). The reaction was conducted for 5 hours, the conversion ratio from effective oil and fat to biodiesel in the system was 98%, and the acid value is 0.3 mg KOH per gram of oil.

Example 2

10 g of lard, 5% of water based on the mass of oil and fat, and 200 standard active units of liquid lipase (derived from *Aspergillus oryzae*) based on the unit mass of oil and fat, were added into single-stage or multi-stage enzyme reactor suitable for enzyme catalysis. The temperature was maintained at 40° C., and methanol with a molar ratio of 6:1 to the oil and fat was evenly added in 4 hours. After 8 hours of reaction, the conversion ratio from effective oil and fat to biodiesel was 91%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The crude biodiesel phase was reflowed into reactor containing immobilized enzyme (containing 200 standard active units of immobilized lipase (derived from *Aspergillus oryzae*) based on the unit mass of oil and fat), and methanol with a molar ratio of 2:1 to the crude biodiesel was simultaneously added. The reaction was conducted, the temperature was maintained at 20° C., and the methanol was added in 1 hour. During the reaction process, the online dehydration as shown in FIG. 2 was conducted (water-absorbing device including organic membrane). The reaction was conducted for 5 hours, the conversion ratio from effective oil and fat to biodiesel in the system was 99%, and the acid value is 0.2 mg KOH per gram of oil.

Example 3

10 g of palm oil, 2% of water based on the mass of oil and fat, and 200 standard active units of liquid lipase (derived from *Thermomyces lanuginosus*) based on the unit mass of oil and fat and 200 standard active units of liquid lipase (derived from *Aspergillus oryzae*) based on the unit mass of oil and fat, were added into single-stage or multi-stage enzyme reactor suitable for enzyme catalysis. The temperature was maintained at 45° C., and ethanol with a molar ratio of 6:1 to the oil and fat was evenly added in 2 hours. After 5 hours of reaction, the conversion ratio from effective oil and fat to biodiesel was 92%. Then the reaction liquid was centrifuged, for stratification, and enzyme-containing heavy phase and crude biodiesel-containing light phase were separated. The heavy phase was further separated by membrane to recover the enzyme, an inorganic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Aspergillus oryzae*) based on the unit mass of oil and fat), and ethanol with a molar ratio of 1:1 to the crude biodiesel was simultaneously added. The reaction was conducted, the temperature was maintained at 20° C., and the ethanol was evenly added in 1 hour. During the reaction process, the online dehydration as shown in FIG. 1 was conducted (water-absorbing device including inorganic membrane). The reaction was conducted for 5 hours, the conversion ratio from effective oil and fat to biodiesel in the system was 98%, and the acid value is 0.4 mg KOH per gram of oil.

Example 4

10 g of yeast oil, 3% of water based on the mass of oil and fat, and 100 standard active units of liquid lipase (derived from *Candida antarctica*) based on the unit mass of oil and fat and 300 standard active units of liquid lipase (derived from *Thermomyces lanuginosus*) based on the unit mass of oil and fat, were added into single-stage or multi-stage enzyme reactor suitable for enzyme catalysis. The temperature was maintained at 50° C., and methanol with a molar ratio of 4:1 to the oil and fat was evenly added in 2 hours. After 5 hours of reaction, the conversion ratio from effective oil and fat to biodiesel was 92%. Then the reaction liquid was maintained in still for stratification, and enzyme-containing heavy phase and crude biodiesel-containing light phase were separated. The heavy phase was further separated by membrane to recover the enzyme, a ceramic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Aspergillus oryzae*) based on the unit mass of oil and fat), and methanol with a molar ratio of 2:1 to the crude biodiesel was simultaneously added. The reaction was conducted, the temperature was maintained at 25° C., and the methanol was evenly added in 1 hour. During the reaction process, the online dehydration as shown in FIG. 2 was conducted (water-absorbing device including ceramic membrane). The reaction was conducted for 5 hours, the conversion ratio from effective oil and fat to biodiesel in the system was 99%, and the acid value is 0.2 mg KOH per gram of oil.

Example 5

10 g of *Jatropha curcas* L. oil, 8% of water based on the mass of oil and fat, and 800 standard active units of liquid lipase (derived from *Candida antarctica*) based on the unit mass of oil, were added into single-stage or multi-stage enzyme reactor suitable for enzyme catalysis. The temperature was maintained at 40° C., and ethanol with a molar ratio of 6:1 to the oil and fat was evenly added in 2 hours. After 5 hours of reaction, the conversion ratio from effective oil and fat to biodiesel was 91%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Thermomyces lanuginosus*) based on the unit mass of oil and fat and 50 standard active units of immobilized lipase (derived from *Candida antarctica*) based on the unit mass of oil and fat), and methanol with a molar ratio of 1:1 to the crude biodiesel was simultaneously added. The reaction was conducted, the temperature was maintained at 30° C., and the methanol was added in 1 hour. During the reaction process, the online dehydration as shown in FIG. 1 was conducted (water-absorbing device including 3 Å molecular sieve). The reaction was conducted for 5 hours, the conversion ratio from effective oil and fat to biodiesel in the system was 99%, and the acid value is 0.3 mg KOH per gram of oil.

Example 6

10 g of fish oil, 20% of water based on the mass of oil and fat, and 500 standard active units of liquid lipase (derived from *Rhizomucor miehei*) based on the unit mass of oil, were added into single-stage or multi-stage enzyme reactor suitable for enzyme catalysis. The temperature was maintained at 55° C., and ethanol with a molar ratio of 6:1 to the oil and fat was evenly added in 3 hours. After 8 hours of reaction, the conversion ratio from effective oil and fat to biodiesel was 91%. Then the reaction liquid was centrifuged for stratification, and enzyme-containing heavy phase and crude biodiesel-containing light phase were separated. The heavy phase was further separated by membrane to recover the enzyme, an inorganic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 400 standard active units of immobilized lipase (derived from *Aspergillus oryzae*) based on the unit mass of oil and fat), and methanol with a molar ratio of 1.5:1 to the crude biodiesel was simultaneously added. The reaction was conducted, the temperature was maintained at 23° C., and the methanol was evenly added in 1 hour. During the reaction process, the online dehydration as shown in FIG. 2 was conducted (water-absorbing device including 4 Å molecular sieve). The reaction was conducted for 5 hours, the conversion ratio from effective oil and fat to biodiesel in the system was 98%, and the acid value is 0.4 mg KOH per gram of oil.

Example 7

10 g of swill oil, 6% of water based on the mass of oil and fat, and 500 standard active units of liquid lipase (derived from *Rhizomucor miehei*) based on the unit mass of oil, were added into single-stage or multi-stage enzyme reactor suitable for enzyme catalysis. The temperature was maintained at 35° C., and ethanol with a molar ratio of 5:1 to the oil and fat was evenly added in 4 hours. After 8 hours of reaction, the conversion ratio from effective oil and fat to biodiesel was 92%, Then the reaction liquid was centrifuged for stratification, and enzyme-containing heavy phase and crude biodiesel-containing light phase were separated. The heavy phase was further separated by membrane to recover the enzyme, a ceramic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 100 standard active units of immobilized lipase (derived from *Aspergillus oryzae*) based on the unit mass of oil and fat and 100 standard active units of immobilized lipase (derived from *Candida antarctica*) based on the unit mass of oil and fat), and ethanol with a molar ratio of 1:1 to the crude biodiesel was simultaneously added. The reaction was conducted, the temperature was maintained at 25° C., and the ethanol was evenly added in 2 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). The reaction was conducted for 7 hours, the conversion ratio from effective oil and fat to biodiesel in the system was 99%, and the acid value is 0.4 mg KOH per gram of oil.

Example 8

10 g of acidified oil, 3% of water based on the mass of oil and fat, and 500 standard active units of liquid lipase (derived from *Aspergillus oryzae*) based on the unit mass of oil, were added into single-stage or multi-stage enzyme reactor suitable for enzyme catalysis. The temperature was maintained at 40° C., and propanol with a molar ratio of 5:1 to the oil and fat was evenly added in 3 hours. After 8 hours of reaction, the conversion ratio from effective, oil and fat to biodiesel was 93%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and methanol with a molar ratio of 2:1 to the crude biodiesel was simultaneously added. The reaction was conducted, the temperature was maintained at 35° C., and the methanol was evenly added in 1 hour. During the reaction process, the online dehydration as shown in FIG. 2 was conducted (membrane dehydration device including organic membrane, and water-absorbing device including 3 Å molecular sieve). The reaction was conducted for 5 hours, the conversion ratio from effective oil and fat to biodiesel in the system was 99%, and the acid value is 0.3 mg KOH per gram of oil.

Example 9

10 g of castor oil, 8% of water based on the mass of oil and fat, and 800 standard active units of liquid lipase (derived from *Candida antarctica*) based on the unit mass of oil, were added into single-stage or multi-stage enzyme reactor suitable for enzyme catalysis. The temperature was maintained at 45° C., and ethanol with a molar ratio of 6:1 to the oil and fat was evenly added in 3 hours. After 6 hours of reaction, the conversion ratio from effective oil and fat to biodiesel was 91%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and methanol with a molar ratio of 1:1 to the crude biodiesel was simultaneously added. The reaction was conducted, the temperature was maintained at 20° C., and the ethanol was added in 2 hours. During the reaction process, the online dehydration as shown in FIG. 1 was conducted (membrane dehydration device including inorganic membrane, and water-absorbing device including 3 Å molecular sieve). The reaction was conducted for 5 hours, the conversion ratio from effective oil and fat to biodiesel in the system was 99%, and the acid value is 0.1 mg KOH per gram of oil.

Example 10

10 g of drainage oil, 12% of water based on the mass of oil and fat, and 2000 standard active units of liquid lipase (derived from *Aspergillus oryzae*) based on the unit mass of oil, were added into single-stage or multi-stage enzyme reactor suitable for enzyme catalysis. The temperature was maintained at 35° C., and methanol with a molar ratio of 5:1 to the oil and fat was evenly added in 2 hours. After 5 hours of reaction, the conversion ratio from effective oil and fat to biodiesel was 93%. Then the reaction liquid was centrifuged for stratification, and enzyme-containing heavy phase and crude biodiesel-containing light phase were separated. The heavy phase was further separated by membrane to recover the enzyme, an inorganic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and ethanol with a molar ratio of 2:1 to the crude biodiesel was simultaneously added. The reaction was conducted, the temperature was maintained at 30° C., and the ethanol was added in 2 hours. During the reaction process, the online dehydration as shown in FIG. 2 was conducted (membrane dehydration device including ceramic membrane, and water-absorbing device including 3 Å molecular sieve). The reaction was conducted for 10 hours, the conversion ratio from effective oil and fat to biodiesel in the system was 99.5%, and the acid value is 0.1 mg KOH per gram of oil.

Example 11

10 g of mutton oil, 6% of water based on the mass of oil and fat, and 1000 standard active units of liquid lipase (derived from *Aspergillus niger*) based on the unit mass of oil, were added into single-stage or multi-stage enzyme reactor suitable for enzyme catalysis. The temperature was maintained at 40° C., and ethanol with a molar ratio of 5:1 to the oil and fat was evenly added in 3 hours. After 8 hours of reaction, die conversion ratio from effective oil and fat to biodiesel was 93%. Then the reaction liquid was centrifuged or maintained in still for stratification, and enzyme-containing heavy phase and crude biodiesel-containing fight phase were separated. The heavy phase was further separated by membrane to recover the enzyme, a ceramic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was re-flowed into immobilized enzyme reactor (containing 100 standard active units of immobilized lipase (derived from *Candida antarctica*) based on the unit mass of oil and fat and 200 standard active units of immobilized lipase (derived from *Aspergillus oryzae*) based on the unit mass of oil and fat), and methanol with a molar ratio of 2:1 to the crude biodiesel was simultaneously added. The reaction was conducted, the temperature was maintained at 25° C., and the methanol was added in 1 hour. During the reaction process, the online dehydration as shown in FIG. 2 was conducted (membrane dehydration device including organic membrane, and water-absorbing device including 4 Å molecular sieve). The reaction was conducted for 8 hours, the conversion ratio from effective oil and fat to biodiesel in the system was 99.5%, and the acid value is 0.2 mg KOH per gram of oil.

Example 12

10 g of swill oil, 12% of water based on the mass of oil and fat, and 600 standard active units of liquid lipase (derived from *Aspergillus niger*) based on the unit mass of oil, were added into single-stage or multi-stage enzyme reactor suitable for enzyme catalysis. The temperature was maintained at 35° C., and methanol with a molar ratio of 6:1 to the oil and fat was evenly added in 3 hours. After 6 hours of reaction, the conversion ratio from effective oil and fat to biodiesel was 92%. Then the reaction liquid was centrifuged or maintained in still for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Rhizomucor miehei*) based on the unit mass of oil and fat), and methanol with a molar ratio of 2:1 to the crude biodiesel was simultaneously added. The reaction was conducted, the temperature was maintained at 20° C., and the methanol was added in 2 hours. During the reaction process, the online dehydration as shown in FIG. 1 was conducted (membrane dehydration device including inorganic membrane, and water-absorbing device including 4 Å molecular sieve). The reaction was conducted for 6 hours, the conversion ratio from effective oil and fat to biodiesel in the system was 99%, and the acid value is 0.2 mg KOH per gram of oil.

Example 13

10 g of *Jatropha curcas* L. oil, 8% of water based on the mass of oil and fat, and 500 standard active units of liquid lipase (derived from *Thermomyces lanuginosus*) based on the unit mass of oil, were added into single-stage or multi-stage enzyme reactor suitable for enzyme catalysis. The temperature was maintained at 45° C., and ethanol with a molar ratio of 6:1 to the oil and fat was evenly added in 4 hours. After 6 hours of reaction, the conversion ratio from effective oil and fat to biodiesel was 92%. Then the reaction liquid was centrifuged or maintained, in still for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and ethanol with a molar ratio of 1:1 to the crude biodiesel was simultaneously added. The reaction was conducted, the temperature was maintained at 25° C., and the ethanol was added in 1 hour. During the reaction process, the online dehydration as shown in FIG. 2 was conducted (membrane dehydration device including ceramic membrane, and water-absorbing device including 4 Å molecular sieve). The reaction was conducted for 5 hours, the conversion ratio from effective oil and fat to biodiesel in the system was 99%, and the acid value is 0.3 mg KOH per gram of oil.

Example 14

10 g of colza oil, 5% of water based on the mass of oil and fat, and 500 standard active units of liquid lipase (derived from *Rhizomucor miehei*) based on the unit mass of oil, were added into single-stage or multi-stage enzyme reactor suitable for enzyme catalysis. The temperature was maintained at 35° C., and ethanol with a molar ratio of 6:1 to the oil and fat was evenly added in 4 hours. After 8 hours of reaction, the conversion ratio from effective oil and fat to biodiesel was 92%. Then the reaction liquid was centrifuged or maintained in still for stratification, and enzyme-containing heavy phase and crude biodiesel-containing light phase were separated. The heavy phase was further separated by membrane to recover the enzyme, an inorganic membrane with a cut-off molecular weight of 15,000 was selected for the recovery of the enzyme, the recovery ratio of enzyme protein was up to 95%, the remaining amount of by-product glycerol in the recovered enzyme liquid was less than 5%), and the recovered enzyme can be reused. The separated crude biodiesel phase was reflowed into immobilized enzyme reactor (containing 100 standard active units of immobilized lipase (derived from *Candida antarctica*) based on the unit mass of oil and fat and 200 standard active units of immobilized lipase (derived from *Rhizomucor miehei*) based on the unit mass of oil and fat), and methanol with a molar ratio of 1:1 to the crude biodiesel was simultaneously added. The reaction was conducted, the temperature was maintained at 25° C., and the methanol was added in 1 hour. During the reaction process, the online dehydration as shown in FIG. 1 was conducted (membrane dehydration device including organic membrane, or inorganic membrane ceramic membrane, and water-absorbing device including 3 Å molecular sieve). The reaction was conducted for 5 hours, the conversion ratio from effective oil and fat to biodiesel in the system was 99%, and the acid value is 0.2 mg KOH per gram of oil.

Example 15

10 g of colza oil, 5% of water based on the mass of oil and fat, and 500 standard active units of liquid lipase (derived from *Aspergillus oryzae*) based on the unit mass of oil, were added into single-stage or multi-stage enzyme reactor suitable for enzyme catalysis. The temperature was maintained at 40° C., and ethanol with a molar ratio of 6:1 to the oil and fat was unevenly added. 30% of the ethanol was evenly added in the first 2 hours of the reaction, and the rest 70% of the ethanol was evenly added in the subsequent 2 hours. After 8 hours of reaction, the conversion ratio from effective oil and fat to biodiesel was 92%. Then the reaction liquid was maintained in still for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and methanol with a molar ratio of 1:1 to the crude biodiesel was simultaneously added. The reaction was conducted, the temperature was maintained at 25° C., and the methanol was added in 1 hour. During the reaction process, the online dehydration as shown in FIG. 2 was conducted (membrane dehydration device including organic membrane or ceramic membrane, and water-absorbing device including 3 Å molecular sieve). The reaction was conducted for 5 hours, the conversion ratio from effective oil and fat to biodiesel in the system was 98%, and the acid value is 0.3 mg KOH per gram of oil.

Example 16

10 g of microalgae oil, 5% of water based on the mass of oil and fat, and 800 standard active units of liquid lipase (derived from *Candida antarctica*) based on the unit mass of oil, were added into single-stage or multi-stage enzyme reactor suitable for enzyme catalysis. The temperature was maintained at 45° C., and ethanol with a molar ratio of 6:1 to the oil and fat was unevenly added. 40% of the ethanol was evenly added in the first 2 hours of the reaction, and the rest 60% of the ethanol was evenly added in the subsequent 2 hours. After 8 hours of reaction, the conversion ratio from effective oil and fat to biodiesel was 90%. Then the reaction liquid was centrifuged for stratification, and enzyme-containing heavy phase and crude biodiesel-containing light phase were separated. The heavy phase was further separated by membrane to recover the enzyme, a ceramic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 100 standard active units of immobilized lipase (derived from *Candida antarctica*) based on the unit mass of oil and fat and 200 standard active units of immobilized lipase (derived from *Rhizomucor miehei*) based on the unit mass of oil and fat), and methanol with a molar ratio of 1:1 to the crude biodiesel was simultaneously added. The reaction was conducted, the temperature was maintained at 25° C., and the methanol was added in 1 hour. During the reaction process, the online dehydration as shown in FIG. 1 was conducted (membrane dehydration device including inorganic membrane or ceramic membrane, and water-absorbing device including 3 Å molecular sieve). The reaction was conducted for 5 hours, the conversion ratio from effective oil and fat to biodiesel in the system was 98%, and the acid value is 0.4 mg KOH per gram of oil.

Example 17

10 g of yellow horn oil, 5% of water based on the mass of oil and fat, and 800 standard active units of liquid lipase (derived from *Candida antarctica*) based on the unit mass of oil, were added into single-stage or multi-stage enzyme reactor suitable for enzyme catalysis. The temperature was maintained at 50° C., and propanol with a molar ratio of 6:1 to the oil and fat was unevenly added. 40% of the propanol was evenly added in the first 2 hours of the reaction, and the rest 60% of the propanol was evenly added in the subsequent 2 hours. After 8 hours of reaction, the conversion ratio from effective oil and fat to biodiesel was 88%. Then the reaction liquid was centrifuged for stratification, and enzyme-containing heavy phase and crude biodiesel-containing light phase were separated. The heavy phase was further separated by membrane to recover the enzyme, a ceramic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*) based on the unit mass of oil and fat), and methanol with a molar ratio of 3:1 to the crude biodiesel was simultaneously added. The reaction was conducted, the temperature was maintained at 25° C., and the methanol was added in 2 hours. During the reaction process, the online dehydration as shown in FIG. 1 was conducted (membrane dehydration device including organic membrane or inorganic membrane, and water-absorbing device including 4 Å molecular sieve). The reaction was conducted for 5 hours, the conversion ratio from effective oil and fat to biodiesel in the system was 98%, and the acid value is 0.5 mg KOH per gram of oil.

Example 18

10 g of sun flower oil, 10% of water based on the mass of oil and fat, and 800 standard active units of liquid lipase (derived from *Aspergillus oryzae*) based on the unit mass of oil, were added into single-stage or multi-stage enzyme reactor suitable for enzyme catalysis. The temperature was maintained at 40° C., and butanol with a molar ratio of 6:1 to the oil and fat was unevenly added. 30% of the butanol was evenly added in the first 2 hours of the reaction, and the rest 70% of the butanol was evenly added in the subsequent 2 hours. After 8 hours of reaction, the conversion ratio from effective oil and fat to biodiesel was 89%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 200 standard active units of immobilized lipase (derived from *Candida antarctica*)

based on the unit mass of oil and fat), and methanol with a molar ratio of 3:1 to the crude biodiesel was simultaneously added. The reaction was conducted, the temperature was maintained at 25° C., and the methanol was added in 2 hours. During the reaction process, the online dehydration as shown in FIG. 1 was conducted (membrane dehydration device including organic membrane or ceramic membrane, and water-absorbing device including 4 Å molecular sieve). The reaction was conducted for 5 hours, the conversion ratio from effective oil and fat to biodiesel in the system was 98%, and the acid value is 0.5 mg KOH per gram of oil.

Example 19

10 g of palm oil, 5% of water based on the mass of oil and fat, and 800 standard active units of liquid lipase (derived from *Candida antarctica*) based on the unit mass of oil, were added into single-stage or multi-stage enzyme reactor suitable for enzyme catalysis. The temperature was maintained at 45° C., and ethanol with a molar ratio of 3:1 to the oil and fat was unevenly added. 40% of the ethanol was evenly added in the first 2 hours of the reaction, and the rest 60% of the ethanol was evenly added in the subsequent 2 hours. After 8 hours of reaction, the conversion ratio from effective oil and fat to biodiesel was 92%. Then the reaction liquid was centrifuged for stratification, and enzyme-containing heavy phase and crude biodiesel-containing light phase were separated. The heavy phase was further separated by membrane to recover the enzyme, an inorganic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 400 standard active units of immobilized lipase (derived, from *Candida antarctica*) based on the unit mass of oil and fat), and methanol with a molar ratio of 2:1 to the crude biodiesel was simultaneously added. The reaction was conducted, the temperature was maintained at 55° C., and the methanol was added in 1 hour. During the reaction process, the online dehydration as shown in FIG. 2 was conducted (membrane dehydration device including organic membrane or ceramic membrane, and water-absorbing device including 4 Å molecular sieve). The reaction was conducted for 5 hours, the conversion ratio from effective oil and fat to biodiesel in the system was 99%, and the acid value is 0.3 mg KOH per gram of oil.

Example 20

10 g of palm oil, 20% of water based on the mass of oil and fat, and 300 standard active units of liquid lipase (derived from *Candida antarctica*) based on the unit mass of oil and 600 standard active units of liquid lipase (derived from *Aspergillus oryzae*) based on the unit mass of oil, were added into single-stage or multi-stage enzyme reactor suitable for enzyme catalysis. The temperature was maintained at 50° C., and ethanol with a molar ratio of 5:1 to the oil and fat was unevenly added. 40% of the ethanol was evenly added in the first 2 hours of the reaction, and the rest 60% of the ethanol was evenly added in the subsequent 2 hours. After 8 hours of reaction, the conversion ratio from effective oil and fat to biodiesel was 91%. Then the reaction liquid was centrifuged for stratification, and enzyme-containing heavy phase and crude biodiesel-containing light phase were separated. The heavy phase was further separated by membrane to recover the enzyme, an organic membrane with a cut-off molecular weight of 15,000 was selected for the recovery of the enzyme, the recovery ratio of enzyme protein was up to 95%, the remaining amount of by-product glycerol in the recovered enzyme liquid was less than 5%, and the recovered enzyme can be reused. The separated crude biodiesel phase was reflowed into immobilized enzyme reactor (containing 100 standard active units of immobilized lipase (derived from *Candida antarctica*) based on the unit mass of oil and fat and 900 standard active units of immobilized lipase (derived from *Rhizomucor miehei*) based on the unit mass of oil and fat), and methanol with a molar ratio of 2:1 to the crude biodiesel was simultaneously added. The reaction was conducted, the temperature was maintained at 40° C., and the methanol was added in 1 hour. During the reaction process, the online dehydration as shown in FIG. 2 was conducted (membrane dehydration device including organic membrane, inorganic membrane, or ceramic membrane, and water-absorbing device including 3 Å or 4 Å molecular sieve). The reaction was conducted for 2 hours, the conversion ratio from effective oil and fat to biodiesel in the system was 99%, and the acid value is 0.2 mg KOH per gram of oil.

The invention is described above in details through general descriptions and specific embodiments, however, based on the invention, some modifications or improvements can still be performed, which is obvious to a person skilled in the art. Accordingly, such modifications or improvements without departing from the spirit of the invention all fall within the protection scope of the invention.

The invention claimed is:

1. A method for preparing biodiesel, wherein said method comprises steps of:

(1) adding oil and fat, short chain alcohol, water, and liquid lipase into a single-stage or multi-stage reactor for conducting a reaction, then separating the reaction liquid into a heavy phase and a light phase; recovering and reusing the liquid lipase in the heavy phase, and using the light phase for subsequent conversion by immobilized lipase;

(2) flowing the light phase obtained in step (1) into a single-stage or multi-stage reactor containing immobilized lipase, and adding short chain alcohol for conducting a reaction; wherein an online dehydration is carried out during the whole reaction or part of the reaction.

2. The method according to claim 1, wherein said method comprises steps of:

(1) adding oil and fat, short chain alcohol of 4-8 times the mole of the oil and fat, 2%-20% of water based on the mass of oil and fat, and 200-2000 standard active units of liquid lipase per gram of oil and fat into the single-stage or multi-stage reactor; maintaining the temperature at 30-55° C.; and conducting the reaction for 3-8 hours;

(2) after the reaction, stratifying the liquid by centrifugation or standing, separating and recovering the enzyme protein in the heavy phase using a membrane, and using the light phase for subsequent conversion by immobilized lipase;

(3) reflowing the light phase obtained in step (2) and short chain alcohol of 1-3 times the mole of the oil and fat into single-stage or multi-stage reactor containing 200-1000 standard active units of immobilized lipase per gram of the mass of oil and fat; maintaining the temperature at 20-55° C.; conducting the reaction for 3-10 hours; wherein an online dehydration with a membrane or a molecular sieve is carried out during the whole reaction or part of the reaction.

3. The method according to claim 2, wherein the membrane used for separating and recovering the enzyme protein in step (2) is a metal membrane, an organic membrane, an inorganic membrane, or a ceramic membrane.

4. The method according to claim 2, wherein the membrane used for the online dehydration in step (3) is an organic membrane, an inorganic membrane, or a ceramic membrane; and wherein the molecular sieve used for the online dehydration is a 3 Å or 4 Å molecular sieve.

5. The method according to claim 1, wherein the lipase is derived from one or more of *Candida antarctica, Thermomyces lanuginosus, Aspergillus niger, Aspergillus oryzae, Rhizomucor miehei*, and *Rhizopus oryzae*.

6. The method according to claim 1, wherein the short chain alcohol is methanol, ethanol, propanol, or butanol.

7. The method according to claim 1, wherein the short chain alcohol is evenly or unevenly fed from the beginning of the reaction, and the feeding is finished in 3-10 hours.

8. The method according to claim 1, wherein the oil and fat is biological oil and fat, including vegetable oil, animal fat, or microbial oil.

9. The method according to claim 8, wherein the vegetable oil is castor oil, palm oil, colza oil, soybean oil, peanut oil, corn oil, cottonseed oil, rice bran oil, *Jatropha* oil, yellow horn oil, or *Jatropha curcas* L. oil; the animal fat is fish oil, tallow, lard, or mutton oil; and the microbial oil is yeast oil or microalgae oil.

10. The method according to claim 1, wherein the oil and fat includes waste cooking oil, or the oil and fat refining waste.

* * * * *